United States Patent [19]
Lane

[11] Patent Number: 5,840,959
[45] Date of Patent: Nov. 24, 1998

[54] METHOD OF OXIDIZING ALKYL-5-FORMYL VALERATE TO MONOALKYL ADIPATE

[75] Inventor: Samuel Livingston Lane, Beaumont, Tex.

[73] Assignees: E. I. du Pont de Nemours and Company, Wilmington, Del.; DSM N.V., Galeen, Netherlands

[21] Appl. No.: 828,974

[22] Filed: Mar. 27, 1997

[51] Int. Cl.$^6$ .................................... C07C 69/34
[52] U.S. Cl. .......................... 560/190; 560/185; 560/191
[58] Field of Search .................................... 560/185, 190, 560/191

[56] References Cited

U.S. PATENT DOCUMENTS

| | | | |
|---|---|---|---|
| 4,537,987 | 8/1985 | Schneider et al. | 560/193 |
| 4,931,590 | 6/1990 | Kummer et al. | 562/590 |

Primary Examiner—Brian M. Burn

[57] ABSTRACT

An improved method for the selective oxidation of alkyl-5-valerate to monomethyl adipate (e.g., methyl-5-valerate to monomethyl adipate). By performing the air oxidation at high pressure (i.e.,>10 bars air and preferably 35 to 65 bars) and relatively moderate temperature (i.e., 20 to 120° C.) in the absence of a catalyst, commercial rates of conversion can be sustained at optimum selectivity to the desired product. Such a high pressure process is particularly amenable to continuous operating the oxidation reactor at optimum selectivity at the expense of conversion per pass followed by product separation and recycle of reactants.

2 Claims, 1 Drawing Sheet

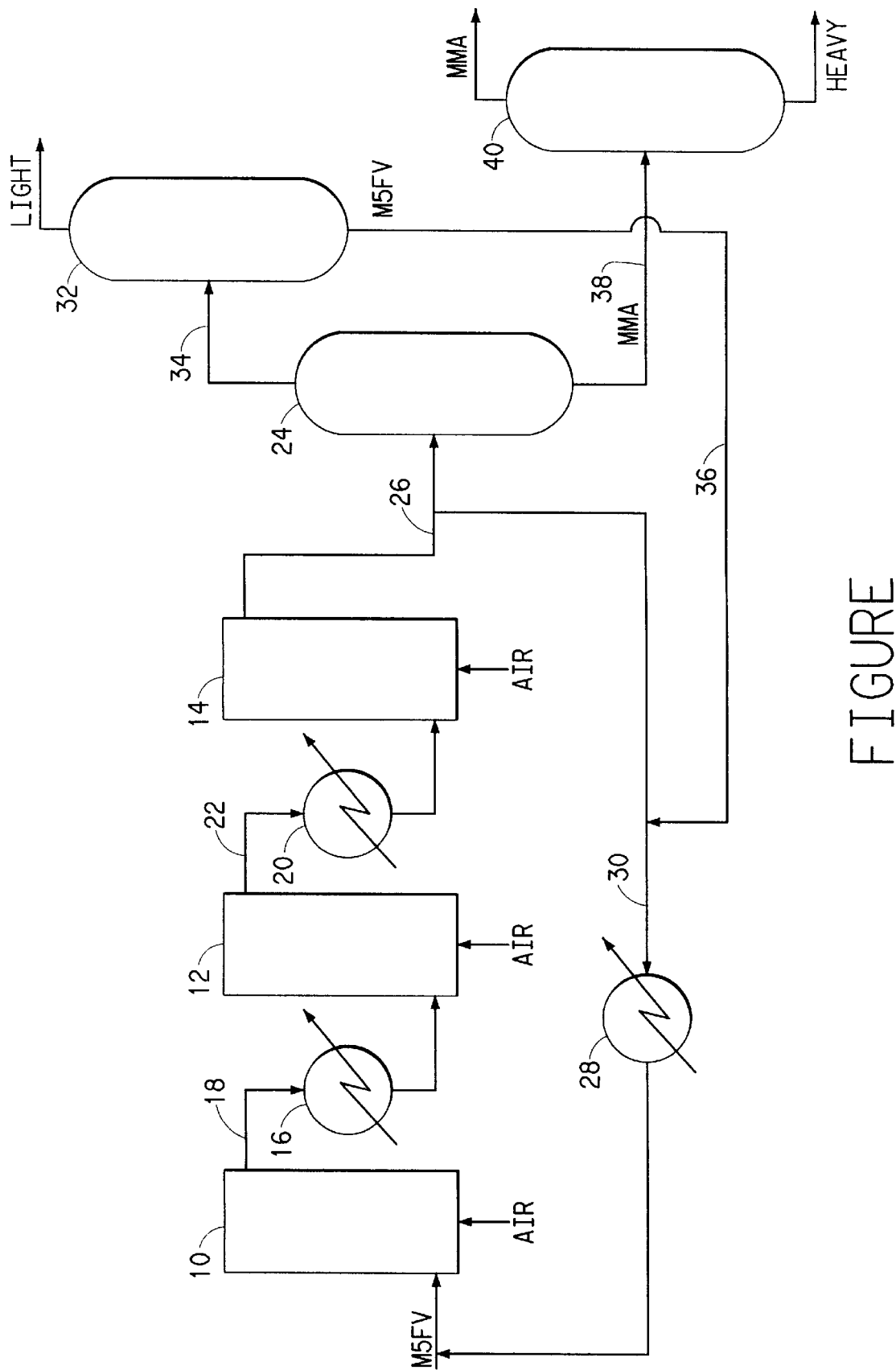
FIGURE

METHOD OF OXIDIZING ALKYL-5-FORMYL VALERATE TO MONOALKYL ADIPATE

BACKGROUND OF THE INVENTION

1. Field of the Invention

This invention relates to an improved process for selectively converting an alkyl-5-formyl valerate to monoalkyl adipate. More specifically but not by way of limitation, the present invention relates to the non-catalytic air oxidation of methyl-5-formyl valerate at high pressure (i.e., in excess of 10 bar).

2. Description of Related Art

It is generally known that the reaction of an ethylenically unsaturated organic compound with carbon monoxide and hydrogen in the presence of a hydroformylation catalyst will produce a terminal aldehyde. It has also been suggested that an alkyl ester of an ethylenically unsaturated organic acid when hydroformylated produces a monoalkyl ester of a corresponding aldehyde terminated homologue. Thus for example, U.S. Pat. Nos. 4,537,987 and 4,931,590 disclose processes for preparing pure monoesters of adipic acid by hydroformylation of a pentenoate in the presence of a carbonyl complex of cobalt or rhodium wherein the 5-formyl valerate is isolated and subsequently oxidized with a molecular oxygen containing gas at 20° C. to 100° C. and a pressure of 1 to 10 bars. Each of these references teach that this oxidation step can be accelerated by adding a catalyst.

SUMMARY OF THE INVENTION

The present invention relates to an improved process for the selective oxidation of an alkyl-5-formyl valerate to a corresponding monoalkyl adipate comprising the steps of:

a) contacting alkyl-5-formyl valerate with a molecular oxygen containing gas at a temperature from 20° C. to 120° C. and at a pressure in excess of 10 bars in the absence of a catalyst for a time sufficient to oxidize the alkyl-5-formyl valerate to monoalkyl adipate; and b) recovering the monoalkyl adipate. In one preferred embodiment of the invention methyl-5-formyl valerate is oxidized with a molecular oxygen containing gas at a temperature from 40° C. to 80° C. and at a pressure of from 35 to 65 bars.

It is an object of this invention to provide a method of preparing monomethyl adipate by non-catalytic air oxidation of methyl-5-formyl valerate in high yields and selectivity at high rates. It is a further object to accomplish this conversion at high selectivity and rate by operating at a high pressure.

BRIEF DESCRIPTION OF THE DRAWING

The FIGURE shows a schematic block drawing of one embodiment of an oxidation plant according to the present invention.

DESCRIPTION OF THE PREFERRED EMBODIMENTS

The present invention relates to an improved process for the selective oxidation of methyl-5-formyl valerate to monomethyl adipate. It has now been discovered that high selectivity at high conversion rates can be achieved by operating at high reactor pressures in the absence of catalyst. In this manner the air oxidation of methyl-5-formyl valerate can be continuously maintained on an industrial scale at high yields of monomethyl adipate.

In contrast to previously suggested methods of oxidizing 5-formyl valeric esters using air at pressures from 1 to 10 bars wherein the presence of a catalyst (e.g. alkali metal hydroxides, or metal salts of cobalt or manganese) is used to accelerate the reaction, the improved method of oxidizing methyl-5-formyl valerate according to the present invention is performed at significantly higher pressure in the absence of catalyst. In fact and as illustrated in the examples, the presence of an oxidation catalyst in the process of the instant invention significantly reduces the selectivity of the desired reaction. Typically to achieve the combination of high selectivity and conversion at commercially feasible reaction rates the reactor must be operated at pressures well in excess of 10 bars of air. Preferably the total pressure when employing air should be in the range of about 20 bars or greater. In principle there is no known upper limit to the acceptable operating pressure. As will be illustrated in the accompanying examples, by employing an operating range of from 35 bars to 65 bars air, very high selectivity and very high conversion are consistently observed at significantly reduced reaction times relative to operating at pressures below 10 bars. Based on higher equipment cost associated with higher operating pressures, a pressure range of 20 to 40 bars air represents a pragmatic and commercially acceptable operating range.

The advantages of the improved process according to the present invention (in particular high selectivity at high conversion rates) can generally be achieved over a temperature range of from about 20° C. to as high as about 120° C. Preferably the improved process is commercially employed at a temperature range of about 40° C. up to about 80° C. Since the oxidation reaction is exothermic, operating a commercial scale reactor at about 50° C. and above is preferred in that heat removal and associated cost become a pragmatic economic consideration (i.e., normal, low-cost cooling water can be used). This is felt to be the pragmatically preferred temperature even though lower temperatures favor higher yields by virtue of reducing the rate of production of undesirable by-products such as methyl valerate, monomethyl glutarate, aldol condensates and methyl-4-formylbutyrate. However it should be appreciated that the overall rate of reaction is also a function of temperature and as will be illustrated in the accompanying examples, temperatures near the lower limit favor the use of higher pressures to achieve correspondingly shorter reaction times (i.e., increased reaction rates caused by increase pressure). As such, operating commercially at higher pressures nearer the lower limit of about 50° C. is viewed as an optimum balance between cost of equipment and acceptable reaction rates without sacrificing selectivity to the desired oxidation product.

The actual method of commercially implementing the improved process according to the present invention can be by any non-catalytic, heterophase, air oxidation methodology as generally known in the art, including by way of example but not by limitation; batch reactor with or without stirring, continuous reactor with plug flow or back-mixing, counter current reactor and the like. Because of the pragmatic considerations associated with heat removal at acceptable reaction rates while optimizing selectivity, the novel process of the instant invention is envisioned as being particularly amenable to continuous or pseudo-continuous operations at about 50° C. and 20 to 40 bars air wherein each, pass through the reactor maintains an optimum selectivity at a conversion perhaps less than optimum with product separation/isolation and substantial recycle of unreacted air/reactants.

The FIGURE illustrates schematically one such preferred commercial embodiment according to the present invention wherein a series of three bubble column air oxidizers 10, 12, and 14 are continuously operated with a feed temperature of typically 50° C. Methyl-5-formyl valerate (M5FV) is introduced at the bottom of air oxidizer 10 along with air. The effluent from the top of column 10 is passed through heat exchanger/cooler 16 via line 18 such as to bring the temperature back to approximately 50° C. (i.e., typically cooling from about 60° C.). The reaction mixture is then directed to the bottom of air oxidizer column 12 which is operated in a manner analogous to column 10. The effluent from column 12 is directed through cooler 20 via line 22 and delivered to the bottom of column 14. The overhead effluent from column 14 is split such that a portion is directed to distillation column 24 via line 26 and the remainder is recycled through cooler 28 via line 30 back to the bottom of air oxidizer 10. Distillation column 24 separates the unreacted methyl-5-formyl valerate and light by-products from the desired monomethyl adipate (MMA) and heavy by-products. The overhead from distillation column 24 is directed to distillation column 32 via line 34 wherein the light by-products are removed from the top of column 32 and the unreacted methyl-5-formyl valerate is recycled via line 36 through cooler 28 (via line 30) before re-entering the bottom of air oxidizer 10. The product stream from the bottom of distillation column 24 is directed via line 38 to distillation column 40 wherein the heavy by-products are separated from the monomethyl adipate. It should be appreciated that the FIGURE is schematic and that various valves, sensors, compressors and other ancillary equipment, all as generally known in the art, are envisioned as being present.

The following examples are presented to more fully demonstrate and further illustrate various individual aspects and features of the present invention while the comparative examples (pressures under 10 bars air) and showings are intended to further illustrate the differences and advantages of the present invention relative to that previously suggested. As such the examples are felt to be non-limiting and are meant to illustrate the invention but are not meant to be unduly limiting in any way.

EXAMPLE 1

A 25 ml glass lined shaker tube was charged with 2.0 grams (~2 ml) of methyl-5-formyl valerate (M5FV) having a purity of 99.2%. The shaker tube was then pressured up to 61 bars (the desired reaction pressure) with nitrogen. Air was purged from the system with a continuous nitrogen flow for 20 minutes. The nitrogen was then stopped and the tube was heated to 80° C. over a period of 13 minutes. Air was introduced to the tube at a rate of 0.2 L/min. The temperature was maintained at 80° C. with shaker agitation for a period of one hour. The heat was shut off and the air flow was switched to nitrogen flow to quench the reaction. The shaker tube was allowed to cool to 30° C. and then the contents were removed. The reactor product was analyzed by gas chromatography yielding the following results presented in Table I.

TABLE I

| Run No. | Temp. (C.) | Pressure (bar) | Reaction Time (hr) | % M5FV Conversion | % Yield Monomethyl adipate |
|---|---|---|---|---|---|
| 1 | 80 | 61.0 | 1.0 | 99.2 | 95.6 |

Comparative Example

In a manner analogous to Example 1, the run was repeated at a pressure of 6.8 bars and 2.5 hours reaction time (note, high pressure gives a higher conversion in a shorter reaction time). The reactor product was analyzed by gas chromatography yielding the following comparative results presented in Table Ia.

TABLE Ia

| Run No. | Temp. (C.) | Pressure (bar) | Reaction Time (hr) | % M5FV Conversion | % Yield Monomethyl adipate |
|---|---|---|---|---|---|
| Comp. 1 | 80 | 7.7 | 2.5 | 27.0 | 92.9 |

EXAMPLE 2

Again in a manner analogous to Example 1, a series of six uncatalyzed air oxidations of methyl-5-formyl valerate were performed at a temperature of 50° C. with reaction time of 2.0 hours and at varying pressures. The observed selectivity and conversion data are presented in Table II

TABLE II

| Run No. | Temp. (C.) | Pressure (bar) | % MMA Selectivity | % M5FV Conversion |
|---|---|---|---|---|
| 1 | 50 | 1.0 | 95.0 | 5.0 |
| 2 | 50 | 10.0 | 97.2 | 21.9 |
| 3 | 50 | 20.0 | 97.8 | 50.3 |
| 4 | 50 | 35.0 | 98.1 | 97.7 |
| 5 | 50 | 50.0 | 98.1 | 98.7 |
| 6 | 50 | 65.0 | 98.3 | 98.9 |

An additional series of six catalyzed air oxidations of methyl-5-formyl valerate were performed at a temperature of 50° C., 2.0 hour reaction time and at varying pressures for comparison. In each run 1,000 ppm cobalt acetylacetonate was added as catalyst. The observed decreased selectivity along with conversion data are presented in Table IIa.

TABLE IIa

| Run No. | Temp. (C.) | Pressure (bar) | % MMA Selectivity | % M5FV Conversion |
|---|---|---|---|---|
| 7 | 50 | 1.0 | 60.7 | 7.6 |
| 8 | 50 | 10.0 | 61.8 | 57.3 |
| 9 | 50 | 20.0 | 66.3 | 95.4 |
| 10 | 50 | 35.0 | 71.9 | 99.6 |
| 11 | 50 | 50.0 | 71.8 | 99.7 |
| 12 | 50 | 65.0 | 72.8 | 99.8 |

Another series of six uncatalyzed air oxidations of methyl-5-formyl valerate were performed at low pressure for two hours and varying temperatures. The observed selectivity and conversion data are presented in Table II TABLE IIb

| Run No. | Temp. (C.) | Pressure (bar) | % MMA Selectivity | % M5FV Conversion |
| --- | --- | --- | --- | --- |
| 13 | 27 | 7.8 | 98.9 | 38.6 |
| 14 | 40 | 7.8 | 98.3 | 40.9 |
| 15 | 50 | 7.8 | 95.3 | 42.2 |
| 16 | 60 | 7.8 | 92.0 | 46.8 |
| 17 | 80 | 7.8 | 88.4 | 46.4 |
| 18 | 100 | 7.8 | 87.0 | 48.7 |

Having thus described and exemplified the invention with a certain degree of particularity, it should be appreciated that the following claims are not to be so limited but are to be afforded a scope commensurate with the wording of each element of the claim and equivalents thereof.

I claim:

1. A method for the selective oxidation of alkyl-5-formyl valerate to monoalkyl adipate comprising the steps of:

a) contacting alkyl-5-formyl valerate with a molecular oxygen containing gas at a temperature from 20° C. to 120° C. and at a pressure in excess of 10 bars in the absence of a catalyst for a time sufficient to oxidize alkyl-5-formyl valerate to monoalkyl adipate; and b) recovering said monoalkyl adipate.

2. A method of claim 1 wherein methyl-5-formyl valerate is contacted with a molecular oxygen containing gas at a temperature from 40° C. to 80° C. and at a pressure of from 35 to 65 bars and monomethyl adipate is recovered.

* * * * *